United States Patent
DiBianca et al.

(10) Patent No.: US 7,453,978 B1
(45) Date of Patent: Nov. 18, 2008

(54) VARIABLE RESOLUTION X-RAY CT DETECTOR WITH MULTI-AXIS TILT

(75) Inventors: Frank A. DiBianca, Memphis, TN (US); Lawrence M. Jordan, Washington, DC (US)

(73) Assignee: University of Tennessee Research Foundation, Knoxville, TN (US)

( * ) Notice: Subject to any disclaimer, the term of this patent is extended or adjusted under 35 U.S.C. 154(b) by 0 days.

(21) Appl. No.: 11/767,613

(22) Filed: Jun. 25, 2007

(51) Int. Cl.
*G01N 23/00* (2006.01)
(52) U.S. Cl. .......................... 378/19; 378/4; 378/98.8
(58) Field of Classification Search ............... 378/4–20, 378/62, 98.8
See application file for complete search history.

(56) References Cited

U.S. PATENT DOCUMENTS

| | | | |
|---|---|---|---|
| 4,417,354 A | 11/1983 | Pfeiler | |
| 4,429,227 A | 1/1984 | DiBianca et al. | |
| 6,285,739 B1 | 9/2001 | Rudin et al. | |
| 6,335,957 B1 | 1/2002 | DiBianca | |
| 6,428,206 B1 * | 8/2002 | Watanabe | 378/197 |
| 6,725,078 B2 | 4/2004 | Bucholz et al. | |

* cited by examiner

*Primary Examiner*—Jurie Yun
(74) *Attorney, Agent, or Firm*—Luedeka, Neely & Graham, P.C.

(57) ABSTRACT

A variable-resolution x-ray (VRX) scanner apparatus forms Computed Tomographic (CT) x-ray images of a subject. The detector array comprises a plurality of detector cells that detect the x-ray radiation at a spatial resolution that is dependent at least in part on cell-to-cell spacing in the array and the orientation of the array with respect to the X-axis and Z-axis. The detector array is operable to be tilted with respect to the Z-axis. The tilt angle of the array, which is preferably 45 degrees, defines an angular relationship between the Z-axis and a pivot axis of the array, where the pivot axis passes through the origin of the XYZ coordinate system. The detector array is operable to be pivoted about the pivot axis and positioned at a pivot angle with respect to the X-axis. The pivot angle defines an angular relationship between the detector array and the X-axis.

13 Claims, 9 Drawing Sheets

ψ = 30, α = 45, β = +90

ψ = 30, α = 45, β = -90

ψ = 30, α = 45, β = +90

ψ = 30, α = 45, β = -90

$\psi = 30, \ \alpha = 45, \ \beta = +90$ $\psi = 30, \ \alpha = 45, \ b = -90$ $\psi = 90, \alpha = 0$

VARIABLE RESOLUTION X-RAY CT DETECTOR WITH MULTI-AXIS TILT

The present invention was developed at least in part with funding received from the National Institutes of Health under grant number EB-00418. The U.S. government may have certain rights in this invention.

This application claims priority to co-pending U.S. patent application Ser. No. 11/672,071 filed Feb. 7, 2007, titled VARIABLE RESOLUTION X-RAY CT DETECTOR WITH TARGET IMAGING CAPABILITY which claims priority to provisional patent application Ser. No. 60/771,177 filed Feb. 7, 2006, titled VARIABLE RESOLUTION X-RAY CT DETECTOR WITH TARGET IMAGING CAPABILITY. The entire disclosure of these prior applications is incorporated herein by reference.

FIELD

This invention relates to the field of Computed Tomographic (CT) x-ray scanners. More particularly, this invention relates to a Variable Resolution (VRX) CT x-ray scanner. According to the invention, the spatial resolution over a portion of a target zone can be greatly increased by tilting a flat panel detector array in multiple directions.

BACKGROUND

Computed Tomographic x-ray scanners (referred to herein as "CT scanners") have been in clinical use since the early 1970s. Generally, a CT scanner uses a rotating x-ray beam and detector to make cross-sectional (or three-dimensional) images of human anatomy and other subjects. In prior CT scanners using flat panel detector arrays, the spatial resolution in the X-Y plane of the resulting image has been increased by angulating the detector array about the Z-axis, where the image is formed by rotating the object of the scan about a rotation axis S that is parallel to the Z-axis. This geometry is illustrated in FIGS. 1A-1B and 2A-2B, where FIGS. 1B and 2B depict the face of a detector array 18 viewed in the direction of the X-axis. In FIGS. 1A and 1B, the face of the detector array 18 is orthogonal to the X-axis (parallel to the Y-axis). In FIGS. 2A and 2B, the face of the detector array 18 is at an angle with respect to the X-axis and Y-axis. In this geometry, the axis about which the array 18 is angulated (also referred to herein as the VRX tilt axis) coincides with the Z-axis, and the axis of rotation of the object (also referred to herein as the scan axis S) is parallel to the Z-axis.

Although the CT scanner geometry depicted in FIGS. 2A and 2B provides the ability to increase image spatial resolution in the X-Y plane (scan plane), it does not provide any increase in spatial resolution in the Z-direction. What is needed, therefore, is a VRX-CT x-ray scanner having an improved geometry that provides for increased spatial resolution in the X-Y plane and the Z-direction simultaneously.

SUMMARY

The present invention provides an apparatus for generating x-ray images of a subject. In one embodiment, the apparatus comprises an x-ray radiation source, a tilted detector array and means for processing signals generated by the detector array. The subject is disposed between the x-ray radiation source and the detector array at a location that is on or adjacent a scan axis, where the scan axis is substantially parallel to the Z-axis of an XYZ coordinate system. The x-ray radiation source directs x-ray radiation along a radiation axis toward the subject, where the radiation axis substantially coincides with the X-axis of the XYZ coordinate system. The detector array, which receives the x-ray radiation as altered by the subject, comprises a plurality of detector cells. The detector cells detect the x-ray radiation at a spatial resolution that is dependent at least in part on cell-to-cell spacing in the array and the orientation of the array with respect to the X-axis and Z-axis. The detector array is operable to be tilted with respect to the Z-axis. The tilt angle of the array defines an angular relationship between the Z-axis and a pivot axis of the array, where the pivot axis passes through an origin of the XYZ coordinate system. The detector array is operable to be pivoted about the pivot axis and positioned at a pivot angle with respect to the X-axis. The pivot angle defines an angular relationship between the detector array and the X-axis.

In preferred embodiments, the spatial image resolution of the detector array in a direction parallel to the Y-axis is expressed as:

$$\Delta Y_3 = \Delta Y_1 \times \sin \psi \times \cos \alpha,$$

and the spatial image resolution of the detector array in a direction parallel to the Z-axis is expressed as:

$$\Delta Z_3 = \Delta Z_1 \times \cos \alpha,$$

where $\Delta Y_3$ is the spatial image resolution of the detector array in a direction parallel to the Y-axis, $\Delta Z_3$ is the spatial image resolution of the detector array in a direction parallel to the Z-axis, $\psi$ is the pivot angle (which ranges from about zero degrees to about ninety degrees), $\alpha$ is the tilt angle (which ranges from about zero degrees to about forty-five degrees), $\Delta Y_1$ is a spacing between centers of the detector cells in a direction parallel to the Y-axis for $\psi$ equals ninety degrees and $\alpha$ equals zero degrees, and $\Delta Z_1$ is a spacing between centers of the detector cells in a direction parallel to the Z-axis for $\psi$ equals ninety degrees and $\alpha$ equals zero degrees. In a most preferred embodiment, the tilt angle $\alpha$ is forty-five degrees.

The improvement in resolution of the VRX-CT imaging provided by the various embodiments of the invention has many areas of application including increasing the resolution of structural details in bodily organs, tumors and other neoplasms, vascular structures, bone structure in the spine, long bones and skull, microcalcifications in breast imaging, intervertebral disks, ligaments, tendons and other connective tissues.

BRIEF DESCRIPTION OF THE DRAWINGS

Further advantages of the invention are apparent by reference to the detailed description in conjunction with the figures, wherein elements are not to scale so as to more clearly show the details, wherein like reference numbers indicate like elements throughout the several views, and wherein.

DETAILED DESCRIPTION

Figure 2B:
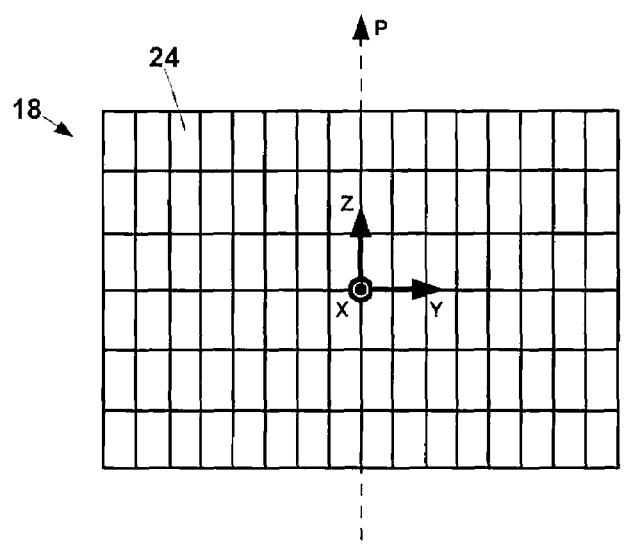
FIG. 2B depicts an X-direction view of the face of a flat panel detector array of FIG. 2A, where the face of the array is at an angle to the Y-axis and the array tilt axis coincides with the Z-axis.
Figure 2A:
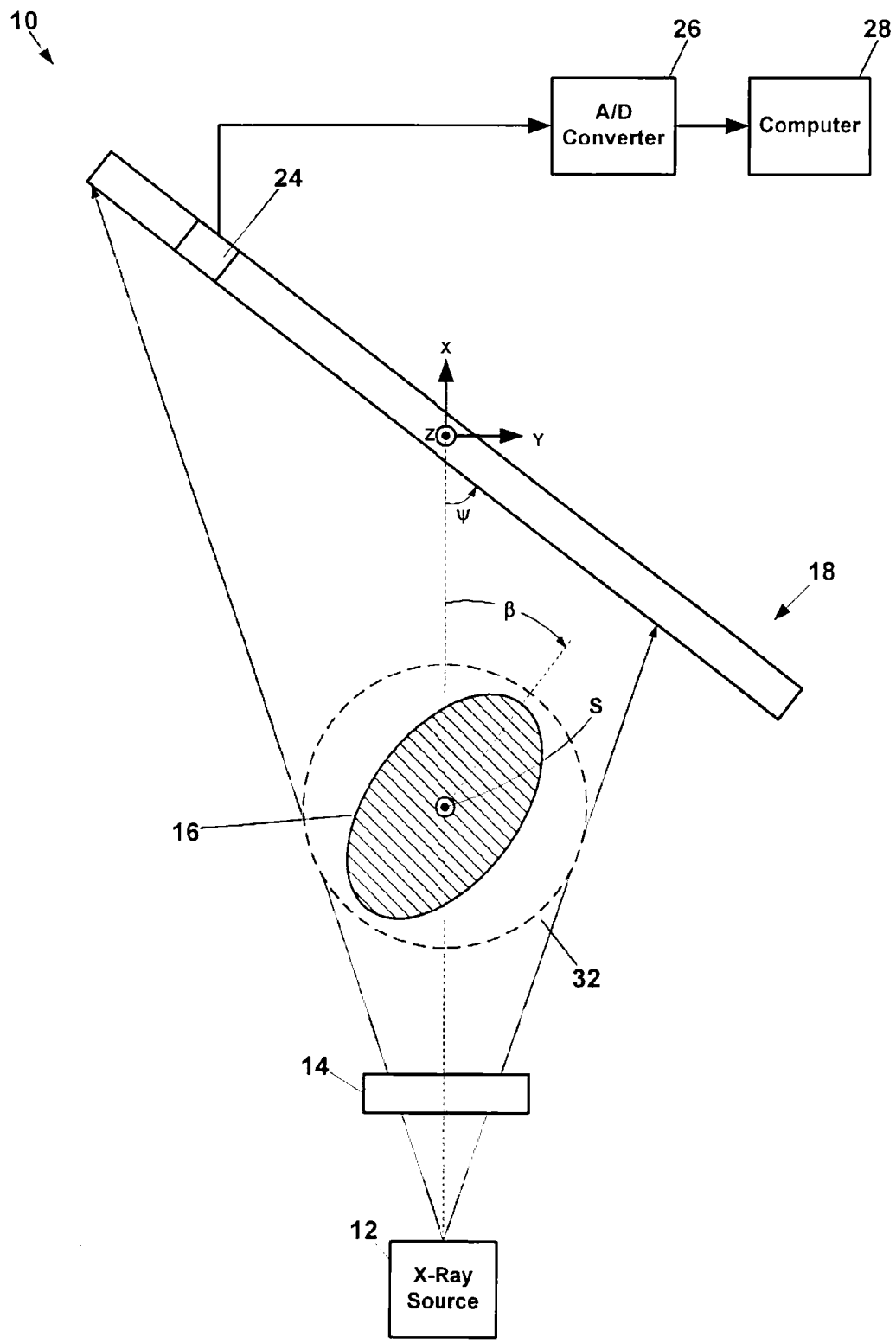
FIG. 2A depicts a Z-direction view of a variable-resolution CT x-ray scanner incorporating a flat panel detector array having a face that is at an angle to the Y-axis.

A preferred embodiment of a two-dimensional flat-panel VRX CT scanner system 10 is shown in FIG. 2A. In this embodiment, the system 10 includes an x-ray radiation source 12, collimator 14, flat-panel detector array 18, analog-digital converter 26 and computer system 28. X-ray radiation from the x-ray source 12 passes through a subject 16 positioned within a scan field 32 between the source 12 and the detector array 18. As described in more detail below, after the x-ray radiation passes through and is modified by the subject 16, the radiation is received and detected by the detector array 18. The analog-digital converter 26 converts the detected analog signals from the detector array 18 into digital signals that are processed by the computer system 28 to generate images of the subject 16.

In one embodiment, a rotating table supports the subject 16 during a scan and rotates the subject 16 about a scan axis S. As shown in FIG. 2A, a scan angle β specifies the rotational orientation of the subject 16 relative to the source axis (X-axis). In another embodiment, the subject 16 remains stationary and the x-ray source 12, collimator 14 and detector array 18 are rotated about the scan axis S. In configurations wherein the A/D converter 26 is physically located with the detector array 18, the A/D converter 26 may also rotate around the subject 16 with the array 18.

In a preferred embodiment, the x-ray source 12 comprises a radiographic x-ray tube, such as model number G-1582BI manufactured by Varian Medical Systems, which operates at a nominal anode input power of about 60 kW with a bias voltage of about 60 kV(peak) and generates a focal spot size of about 0.6 mm. In an alternative embodiment, the x-ray source 12 comprises a micro-focus x-ray tube, such as model SB-80-250 manufactured by Source-Ray, Inc., which operates at about 80 kV(peak) and generates a focal spot size of about 36 μm by 65 μm.

The collimator 14 redirects the x-ray radiation to a specific region of the subject 16 which is projected onto the array 18. In a preferred embodiment, the collimator 14 comprises a multi-slice collimator for directing the x-ray radiation simultaneously to more than one X-Y "slice" of the subject 16.

Figure 1A:
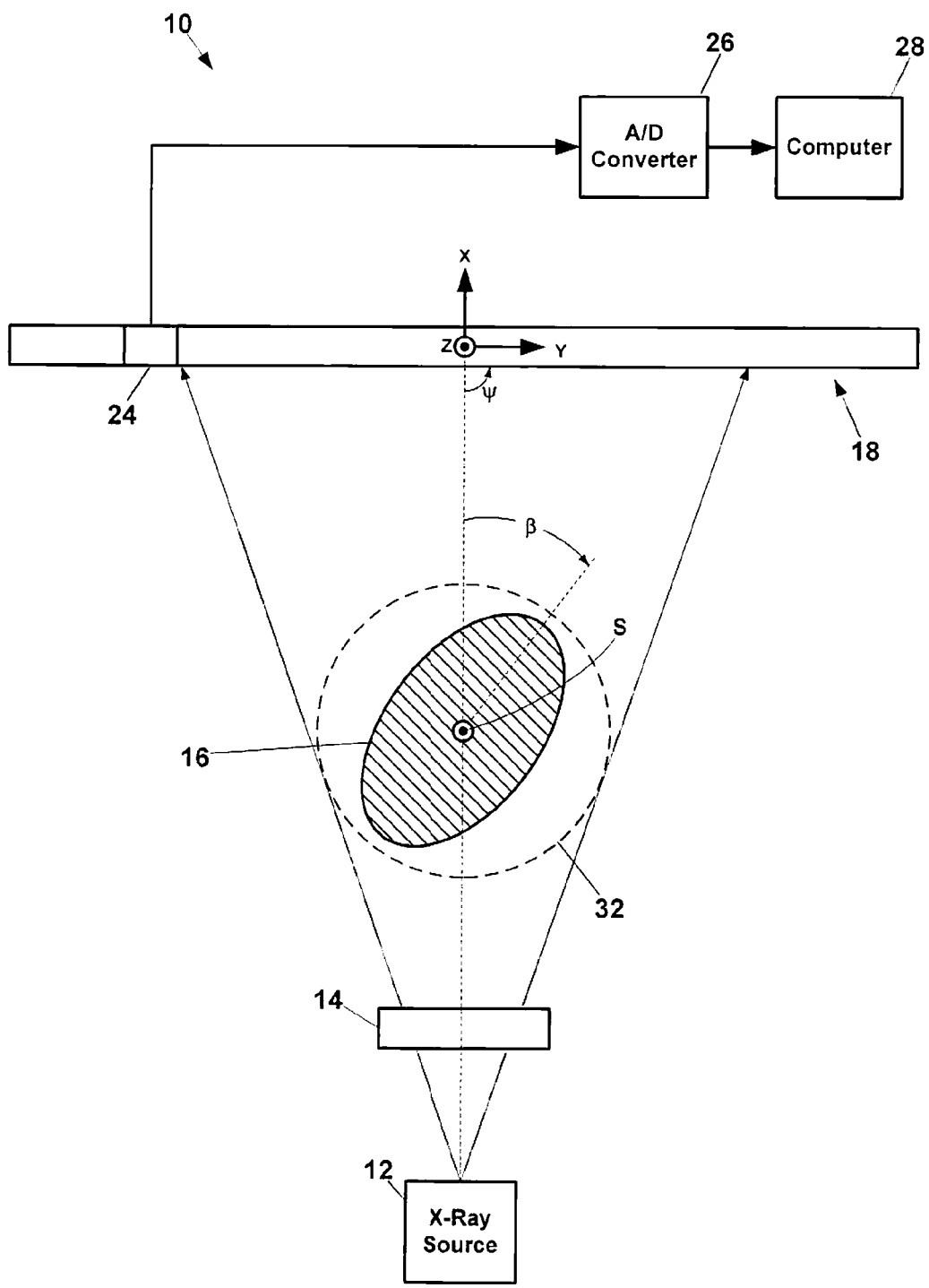
FIG. 1A depicts a Z-direction view of a variable-resolution CT x-ray scanner incorporating a flat panel detector array having a face that is parallel to the Y-axis.
Figure 1B:
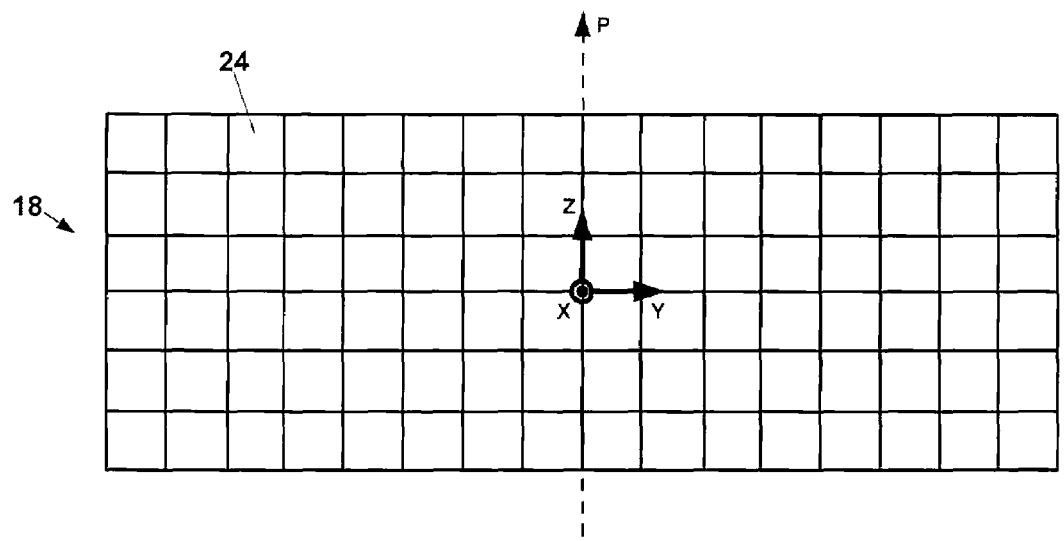
FIG. 1B depicts a X-direction view of the face of the flat panel detector array of FIG. 1A, where the face of the array is parallel to the Y-axis and the array tilt axis coincides with the Z-axis.

In the embodiment of FIG. 2A, the detector array 18 is a flat-panel array of about 30-100 cm in length (which corresponds to the Y-direction in FIG. 1B) and about 30-45 cm in height (which corresponds to the Z-direction in FIG. 1B). In configurations wherein large variations in the pivot angle ψ are needed to obtain a desired resolution, the length of the array 18 will generally be much greater than the height. The detector array preferably comprises a plurality of discrete detector cells 24 arranged in a two-dimensional grid, such as a 1000×1000 cell grid or a 2000×2000 cell grid. The center-to-center spacing of cells in the grid is in the range of about 0.1 to 1 mm, although values outside this range may be required, depending on the use intended. In one exemplary embodiment, each detector cell 24 is a $CdWO_4$ crystal-photodiode scintillator cell. It will be appreciated that the array 18 could comprise any number of cells in any two-dimensional arrangement. Thus, the invention is not limited to any particular number or arrangement of cells in the detector array 18. In the embodiments depicted in the figures herein, the array 18 comprises ninety-six cells arranged in a 6×16 array. So as not to overcomplicate FIG. 2A, only one cell 24 in the top row is depicted.

In general, the maximum scan field of the array 18 is about one half the actual detector active dimension, which corresponds to a magnification of two. A typical 360° scan time is about four seconds using a radiographic x-ray tube for the x-ray source 12 and about 20 seconds using a micro-focus tube.

As shown in FIG. 2A, the analog/digital (A/D) converter 26 receives analog sample signals from the detector cells 24 and converts the analog sample signals into digital sample signals. The digital sample signals are provided to the computer system 28 for image processing. In a preferred embodiment, the A/D converter 26 is a 16-bit device that samples the detector signals every 2.5 mS. As described in more detail below, the computer system 28 executes software applications to calibrate the system 10 and to process the digital sample signals to generate images of the subject 16.

As shown in FIGS. 1B, 1C, 2B and 2C, the array 18 is operable to be pivoted about a pivot axis P (also referred to as the P-axis) which passes through the origin of the XYZ coordinate system shown in the figures. In FIGS. 1B and 2B, the P-axis coincides with the Z-axis. As the array 18 is pivoted about the P-axis, the face of the array is at an pivot angle ψ relative to the X-axis (FIG. 2A), which coincides with the central radiation axis of the source 12. In FIGS. 1A and 1B, the angle ψ is 90 degrees. In FIGS. 2A and 2B, the angle ψ is 45 degrees.

Figure 1C:
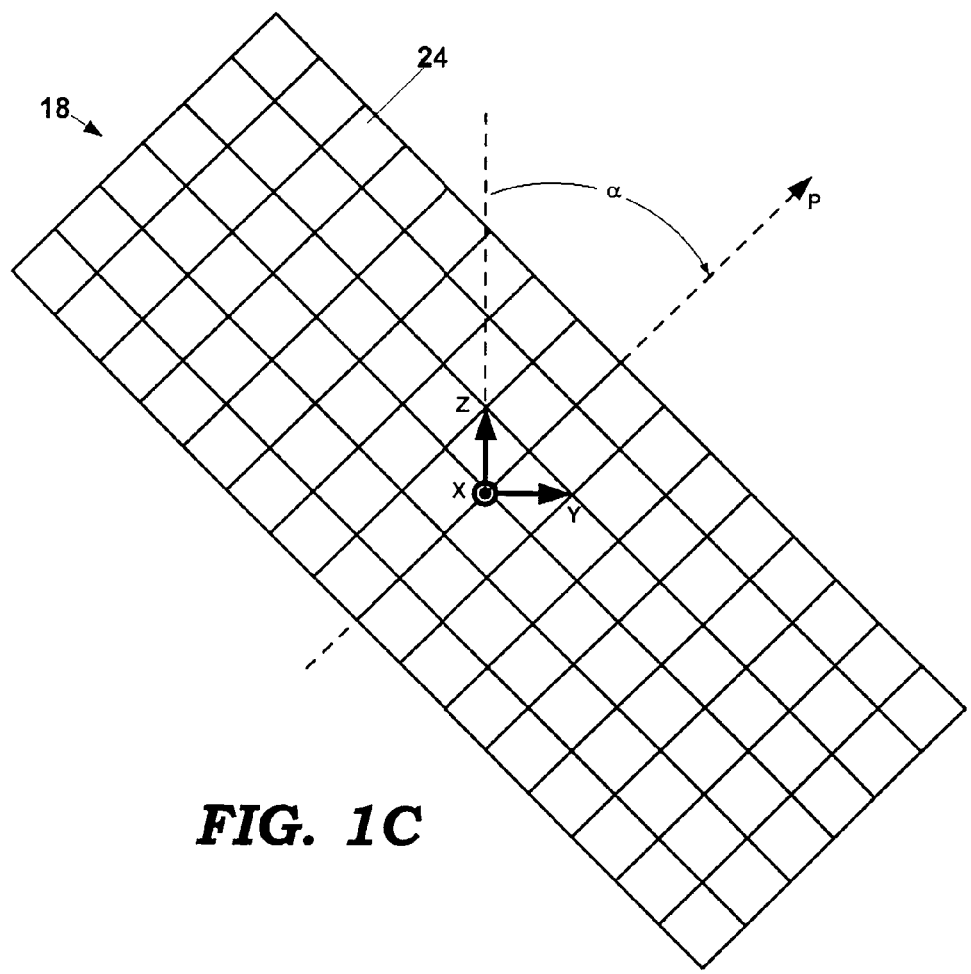
FIG. 1C depicts a X-direction view of the face of the flat panel detector array of FIG. 1A, where the face of the array is parallel to the Y-axis and the array tilt axis is at an angle to the Z-axis.
Figure 2C:
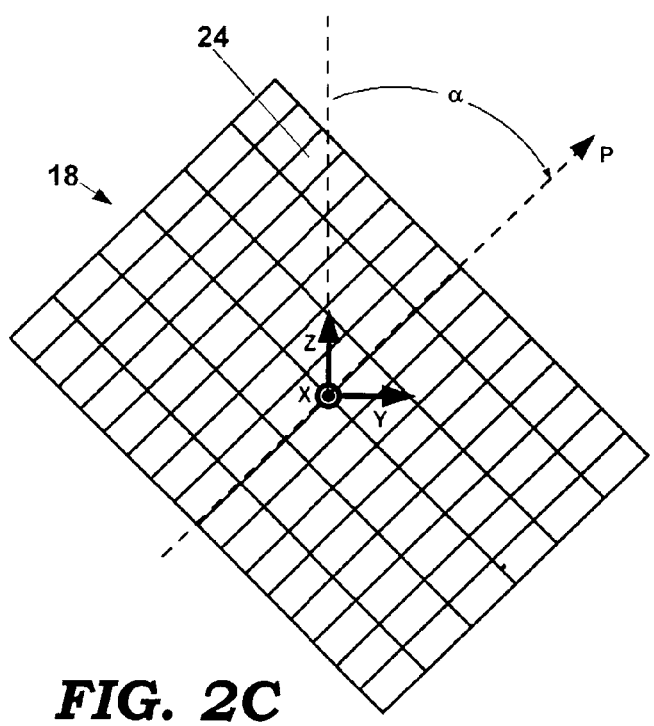
FIG. 2C depicts an X-direction view of the face of the flat panel detector array of FIG. 2A, where the face of the array is at an angle to the Y-axis and the array tilt axis is at an angle to the Z-axis.

In preferred embodiments of the invention, the P-axis is operable to be positioned at a tilt angle α with respect to the Z-axis. In FIGS. 1C and 2C, the tilt angle α is 45 degrees. In FIGS. 1B and 2B, the tilt angle α is 0 degrees.

Figure 3:
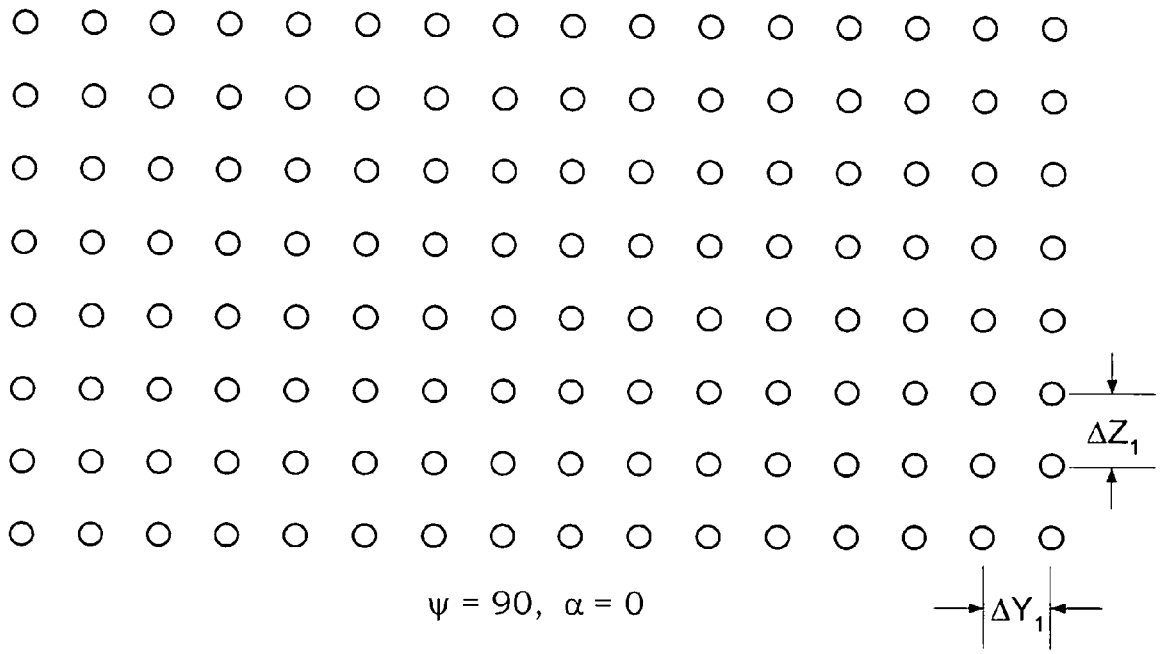
FIG. 3 depicts an X-direction view of the face of the flat panel detector array, where the face of the array is parallel to the Y-axis and the array tilt axis coincides with the Z-axis according to a preferred embodiment of the invention.
Figure 4:
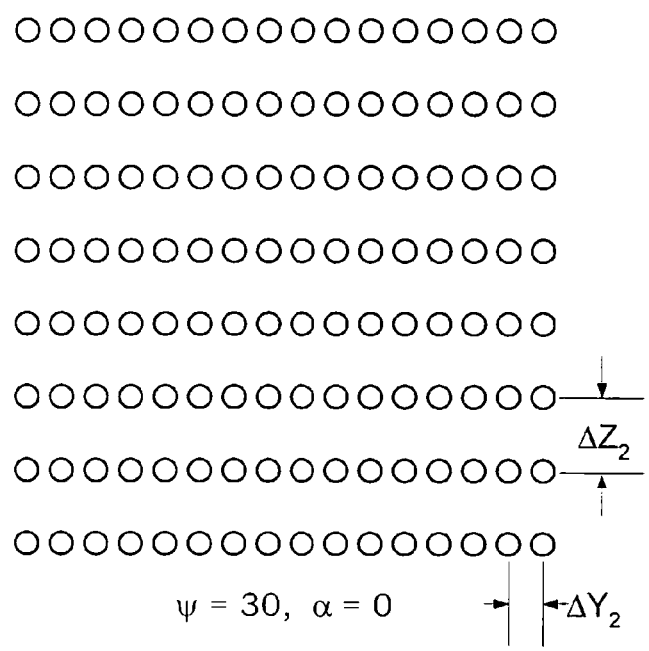
FIG. 4 depicts an X-direction view of the face of a flat panel detector array, where the face of the array is at an angle to the Y-axis and the array tilt axis coincides with the Z-axis according to a preferred embodiment of the invention.

FIGS. 3 and 4 depict the increase in spatial resolution in the CT scan plane (X-Y plane) that results from pivoting the array 18 about the pivot axis P. For purposes of concept illustration, the centers of the detector cells 24 of the array 18 are represented in these figures as circles. In FIG. 3, where the pivot angle ψ is 90 degrees and the tilt angle α is 0 degrees, the projected spatial distance $\Delta Y_1$ between cells in the Y-direction is equivalent to the projected spatial distance $\Delta Z_1$ between cells in the Z-direction. In FIG. 4, where the pivot angle $\psi$ is 30 degrees and the tilt angle $\alpha$ is 0 degrees, the projected spatial distance $\Delta Y_2$ between cells in the Y-direction is reduced relative to the projected spatial distance $\Delta Y_1$ according to:

$$\Delta Y_2 = \Delta Y_1 \times \sin \psi = \Delta Y_1 \times \sin(30) = 0.5 \Delta Y_1. \quad \text{Eq. 1}$$

The reduced projected spacing of cells in the Y-direction results in a reconstructed CT image having an image resolution in the X-Y plane (also referred to as the scan plane or slice plane) that is twice the resolution of an image formed with $\psi$ set to 90 degrees.

FIG. 5 depicts the increase in projected spatial resolution in the Y-Z plane that results from positioning the array 18 such that the pivot axis P is at a tilt angle $\alpha$ of 45 degrees relative to the Z-axis and the pivot angle $\psi$ is 30 degrees. In this case, the projected spatial distance $\Delta Y_3$ between cells in the Y-direction is reduced relative to the projected spatial distance $\Delta Y_2$ (FIG. 4) according to:

$$\Delta Y_3 = \Delta Y_2 \times \cos \alpha = \Delta Y_2 \times \cos(45) = 0.707 \Delta Y_2. \quad \text{Eq. 2}$$

Thus, based on equations 1 and 2 above, the relationship between $\Delta Y_3$ and $\Delta Y_1$ may be expressed as:

$$\Delta Y_3 = \Delta Y_1 \times \sin \psi \times \cos \alpha. \quad \text{Eq. 3}$$

Note in FIG. 5 that the projected spatial distance $\Delta Z_3$ between cells in the Z-direction is reduced relative to the projected spatial distance $\Delta Z_2$ (FIG. 4) according to:

$$\Delta Z_3 = \Delta Z_2 \times \cos \alpha = \Delta Z_2 \times \cos(45) = 0.707 \Delta Z_2 \quad \text{Eq. 4}$$

Also, the relationship between $\Delta Z_3$ and $\Delta Z_1$ may be expressed as:

$$\Delta Z_3 = \Delta Z_1 \times \cos \alpha. \quad \text{Eq. 5}$$

Thus, decreasing the pivot angle $\psi$ of the detector array increases the CT image resolution in the X-Y scan plane (X-Y resolution$\to\infty$ as $\psi\to 0$), and rotating the tilt angle $\alpha$ toward 45 degrees increases the image resolution in the Z-Y plane. Based on the geometry depicted in FIG. 5, the optimum value for $\alpha$ is 45 degrees, as this value provides the best compromise resolution improvement in all three directions (X, Y and Z).

Figure 5A:
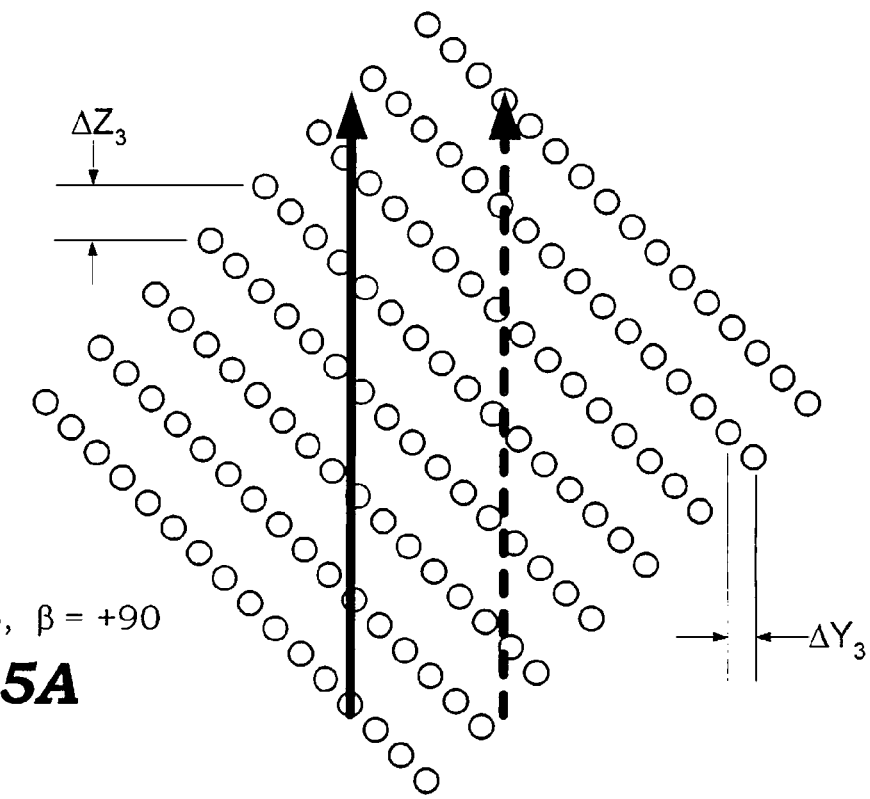
FIGS. 5A and 5B depict an X-direction view of a pair of vertical wires projected onto the face of a flat panel detector array, where the face of the array is at an angle to the Y-axis and the array tilt axis is at an angle to the Z-axis.
Figure 5B:
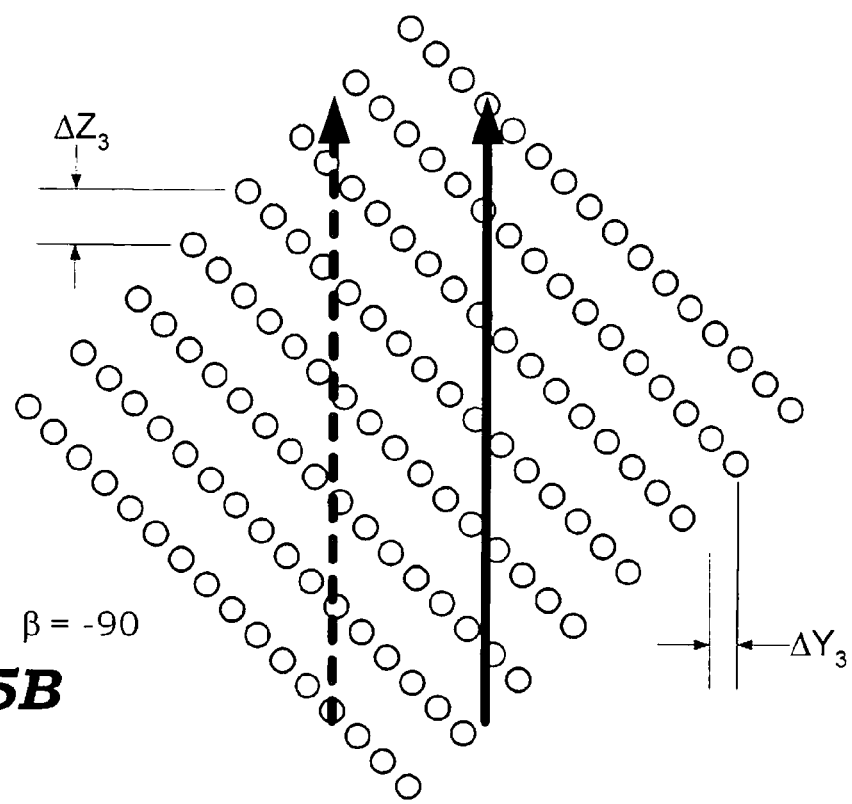
Figure 6A:
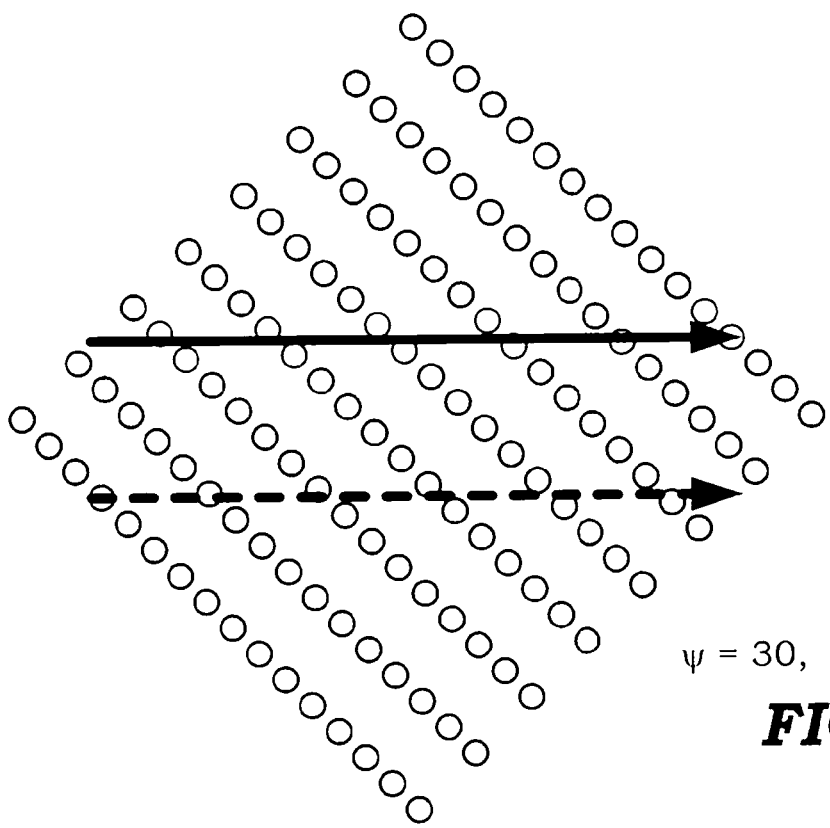
FIGS. 6A and 6B depict an X-direction view of a pair of horizontal wires projected onto the face of a flat panel detector array, where the face of the array is at an angle to the Y-axis and the array tilt axis is at an angle to the Z-axis.
Figure 6B:
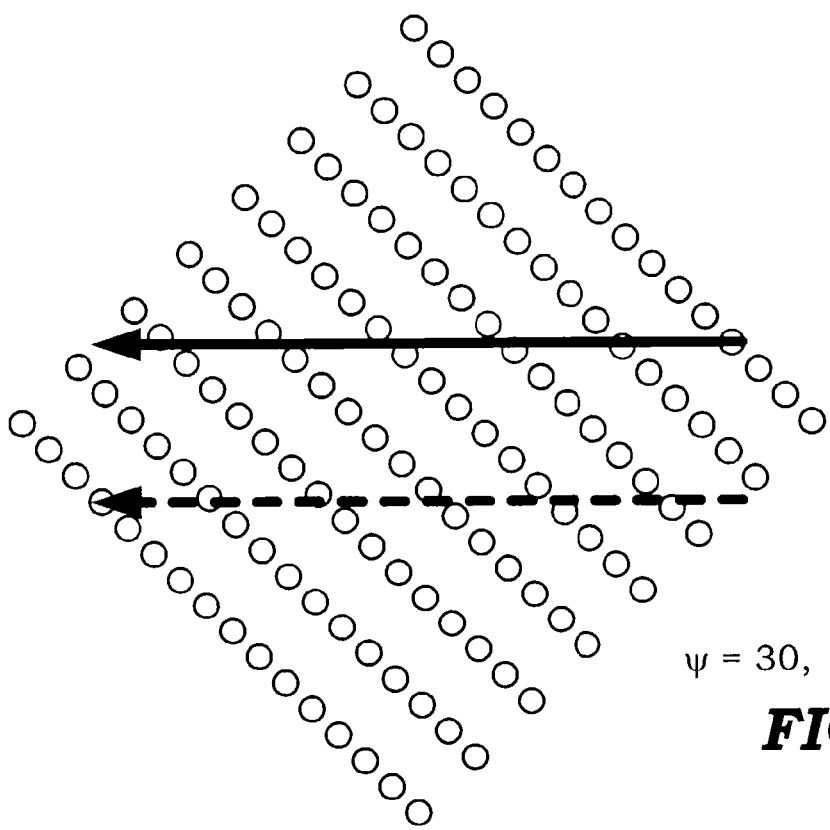
Figure 7A:
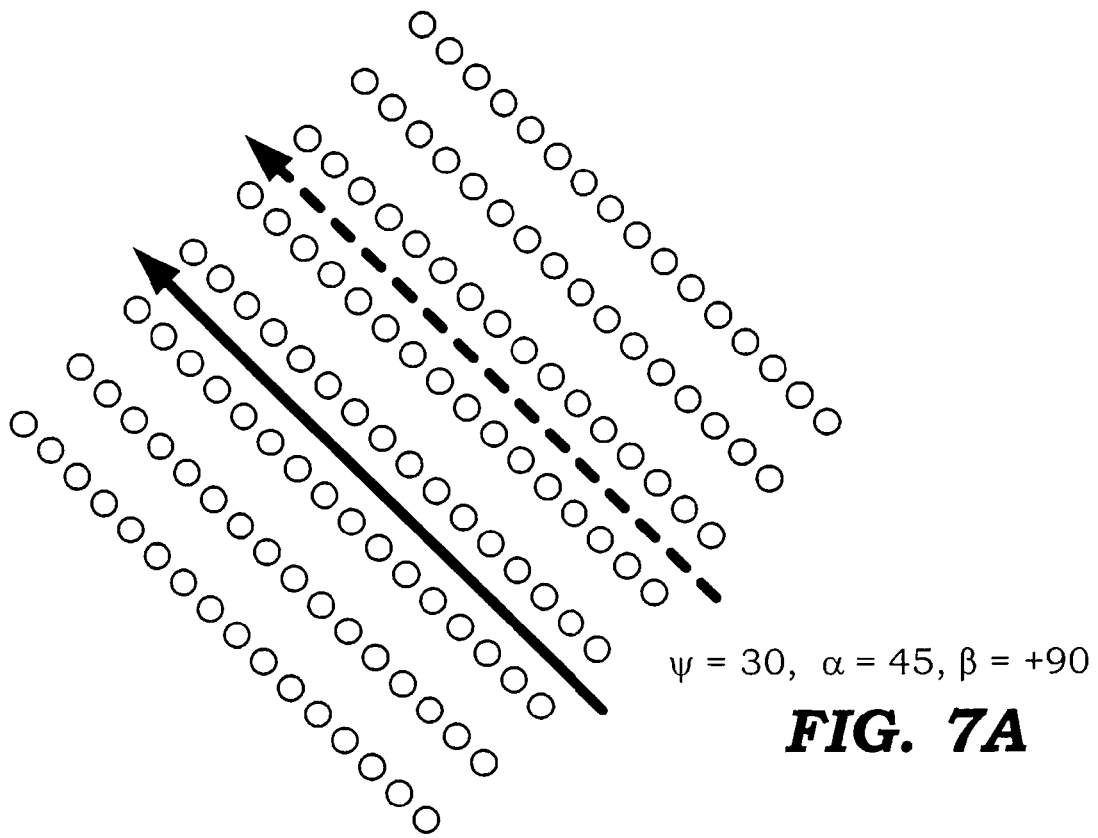
FIGS. 7A and 7B depict an X-direction view of a pair of wires oriented at 45 degrees projected onto the face of a flat panel detector array, where the face of the array is at an angle to the Y-axis and the array tilt axis is at an angle to the Z-axis.
Figure 7B:
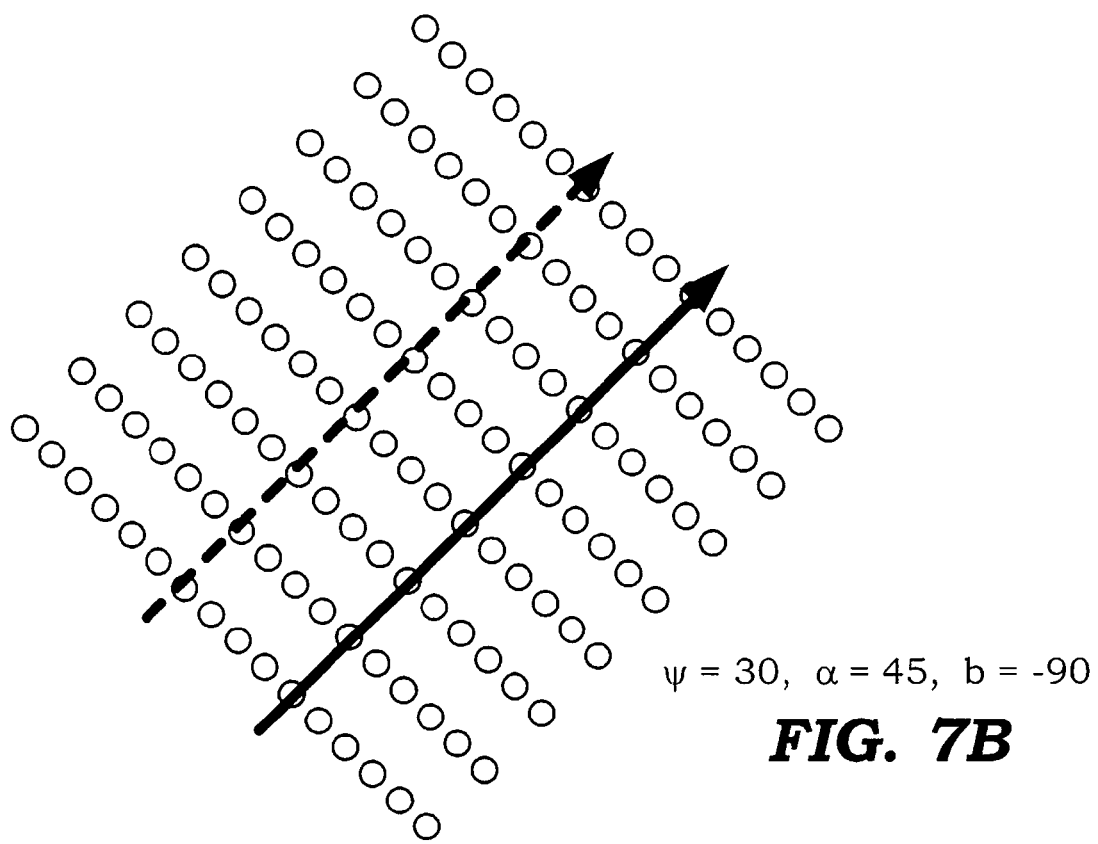

FIGS. 5A-5B, 6A-6B and 7A-7B depict how a simple subject in various orientations may be sampled using a flat-panel detector array tilted to 45 degrees ($\alpha=45°$) and pivoted to 30 degrees ($\psi=30°$). In each case, the subject is a set of two parallel wires (represented by solid and dashed arrows) centered on the axis of rotation S of the scanner system 10. In this example, the subject is rotated about the axis S and the source 12 and array 18 are stationary. In FIGS. 5A and 5B, the wires are parallel to the rotation axis S. In FIGS. 6A and 6B, the wires are orthogonal to the rotation axis S. In FIGS. 7A and 7B, the wires are at a 45 degree angle with respect to the rotation axis S.

In each of the configurations depicted in FIGS. 5A-5B, 6A-6B and 7A-7B, as the wires rotate 180 degrees about the rotation axis S, they are sampled at several points during the rotation. These sample points include positions at which the object scan angle $\beta$ equals +90 (FIGS. 5A, 6A and 7A) and −90 degrees (FIGS. 5B, 6B and 7B). In FIGS. 5A-5B and 6A-6B, it is apparent that the vertical and horizontal wire pairs are resolved at both phases of the scan ($\beta=\pm 90$). In the position depicted in FIG. 7A ($\beta=+90$), the wire pair is not resolved because neither wire is sampled by any of the cells of the array. However, in the position depicted in FIG. 7B ($\beta=-90$), the wire pair is clearly resolved.

Note that if the detector array were tilted such that $\alpha$ equals 90°, the vertical wire pair would not be detected at the $\beta=+90$ scan position or the $\beta=-90$ scan position. If the detector array is not tilted at all ($\alpha=0°$ as shown in FIG. 4), the horizontal wire pair would not be detected at any scan position.

Figure 8:
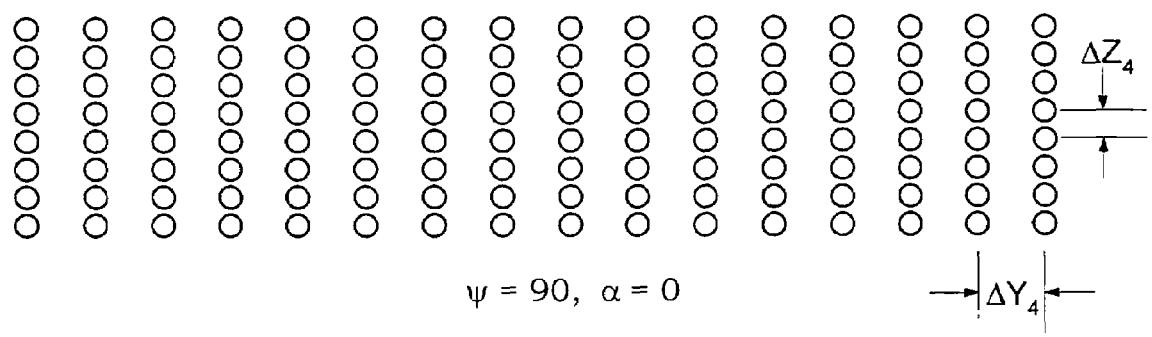
FIG. 8 depicts an X-direction view of the face of the flat panel detector array, where the face of the array is tilted with respect to the Z-axis according to a preferred embodiment of the invention.

It should also be appreciated that if the detector array 18 is tilted about the Y-axis (with the tilt angle $\alpha$ set to zero degrees), the projected spatial image resolution is improved in the Z-direction. This is illustrated in FIG. 8 ($\Delta Z_4 < \Delta Z_1$). However, this configuration does not affect resolution in Y-direction ($\Delta Y_4 = \Delta Y_1$), and therefore provides no resolution enhancement in the X-Y plane of a CT image scan.

Figure 9:
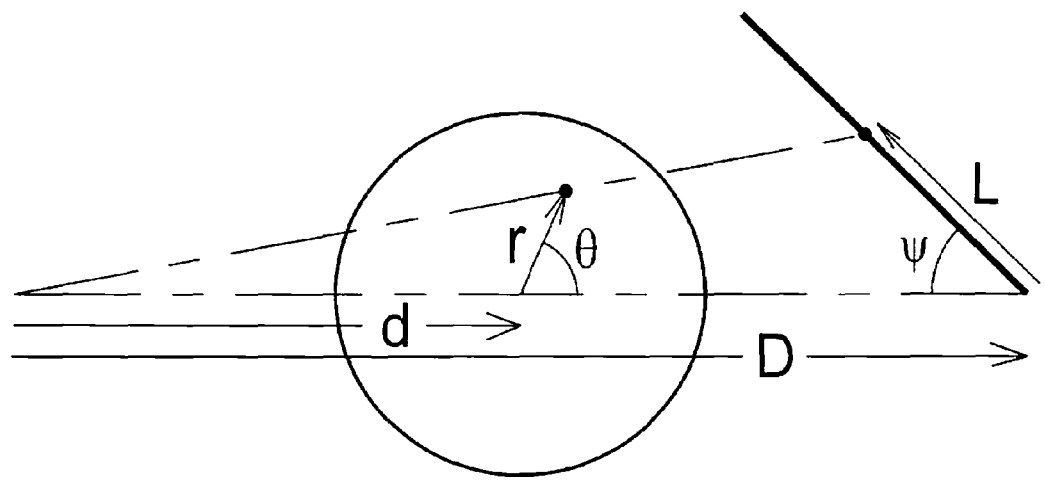
FIG. 9 depicts the mapping of an object point to VRX space according to a preferred embodiment of the invention.

Prior to scanning a subject and constructing images, a calibration procedure is performed to specify the geometry of the detector array. In a preferred embodiment of the invention, the calibration procedure involves moving an x-ray "shadow" of a metal pin across the entire detector array during a scan and mapping the position of the shadow. This may be accomplished by mounting the pin on a rotating platform in the scan field 32, with the pin positioned far enough away from the platform's center of rotation so that the pin's shadow will pass across the entire detector array during a rotation of the platform. A calibration algorithm executed on the computer system 28 determines three geometrical parameters, including the angular rotation and translation of the array in two directions in the scan plane. The calibration mapping equation is expressed as:

$$L = \frac{rD\sin\theta}{r\sin(\theta - \psi) - d\sin\psi},$$

where L, r, D, d, $\theta$ and $\psi$ are depicted in FIG. 9.

The foregoing description of preferred embodiments for this invention has been presented for purposes of illustration and description. They are not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. An apparatus for generating x-ray images of a subject, the apparatus comprising:

an x-ray radiation source for directing x-ray radiation along a radiation axis toward the subject, where the radiation axis substantially coincides with an X-axis of an XYZ coordinate system;

a detector array for receiving the x-ray radiation as altered by the subject, the detector array comprising a plurality of detector cells for receiving and detecting the x-ray radiation at a spatial resolution which is dependent at least in part on cell-to-cell spacing between detector cells in the array and the orientation of the array with respect to the X-axis and Z-axis of the XYZ coordinate system, wherein the detector array is operable to be positioned at a tilt angle with respect to the Z-axis of the XYZ coordinate system, where the tilt angle defines an angular relationship between the Z-axis and a pivot axis of the detector array, where the pivot axis passes through an origin of the XYZ coordinate system, and wherein the detector array is operable to be pivoted about the pivot axis and positioned at a pivot angle with respect to the X-axis of the XYZ coordinate system, where the pivot angle defines an angular relationship between the detector array and the X-axis; and means for processing signals generated by the detector cells of the detector array to generate a human-perceivable image of the subject, wherein the subject is disposed between the x-ray radiation source and the detector array at a location on or adjacent a scan axis of the apparatus, wherein the scan axis is substantially parallel to the Z-axis.

2. The apparatus of claim 1 further comprising means for rotating the subject about the scan axis as the detector array and x-ray radiation source remain stationary.

3. The apparatus of claim 1 further comprising means for moving the detector array and x-ray radiation source about the scan axis as the subject remains stationary.

4. The apparatus of claim 1 further comprising a collimator for directing at least a portion of the x-ray radiation to the subject.

5. The apparatus of claim 1 wherein the spatial image resolution of the detector array in a direction parallel to the Y-axis is expressed as:

$$\Delta Y_3 = \Delta Y_1 \times \sin \psi \times \cos \alpha,$$

wherein
$\Delta Y_3$ is the spatial image resolution of the detector array in a direction parallel to the Y-axis,
$\psi$ is the pivot angle,
$\alpha$ is the tilt angle, and
$\Delta Y_1$ is a spacing between centers of the detector cells in a direction parallel to the Y-axis for a condition wherein $\psi$ equals ninety degrees and a equals zero degrees.

6. The apparatus of claim 1 wherein the spatial image resolution of the detector array in a direction parallel to the Z-axis is expressed as:

$$\Delta Z_3 = \Delta Z_1 \times \cos \alpha,$$

wherein
$\Delta Z_3$ is the spatial image resolution of the detector array in a direction parallel to the Z-axis,
$\alpha$ is the tilt angle, and
$\Delta Z_1$ is a spacing between centers of the detector cells in a direction parallel to the Z-axis for a condition wherein a equals zero degrees and the pivot angle equals ninety degrees.

7. The apparatus of claim 1 wherein the pivot angle has a value ranging from about zero degrees to about ninety degrees.

8. The apparatus of claim 1 wherein the tilt angle has a value ranging from about zero degrees to about 45 degrees.

9. The apparatus of claim 1 wherein the tilt angle has a value of 45 degrees.

10. The apparatus of claim 1 wherein the detector cells comprise $CdWO_4$ crystal-photodiode scintillator cells.

11. The apparatus of claim 1 wherein the detector array comprises a flat panel detector array.

12. The apparatus of claim 1 wherein the detector array is rectangular.

13. An apparatus for generating x-ray images of a subject, the apparatus comprising:

an x-ray radiation source for directing x-ray radiation along a radiation axis toward the subject, where the radiation axis substantially coincides with an X-axis of an XYZ coordinate system;

a rectangular detector array for receiving the x-ray radiation as altered by the subject, the detector array comprising a plurality of detector cells for receiving and detecting the x-ray radiation at a spatial resolution which is dependent at least in part on cell-to-cell spacing between detector cells in the array and the orientation of the array with respect to the X-axis and Z-axis of the XYZ coordinate system, wherein the detector array is operable to be positioned at a tilt angle with respect to the Z-axis of the XYZ coordinate system, where the tilt angle defines an angular relationship between the Z-axis and a pivot axis of the detector array, where the pivot axis passes through an origin of the XYZ coordinate system, and wherein the detector array is operable to be pivoted about the pivot axis and positioned at a pivot angle with respect to the X-axis of the XYZ coordinate system, where the pivot angle defines an angular relationship between the detector array and the X-axis;

wherein the spatial image resolution of the detector array in a direction parallel to the Y-axis is expressed as:

$$\Delta Y_3 = \Delta Y_1 \times \sin \psi \times \cos \alpha, \text{ and}$$

wherein the spatial image resolution of the detector array in a direction parallel to the Z-axis is expressed as:

$$\Delta Z_3 = \Delta Z_1 \times \cos \alpha,$$

where
$\Delta Y_3$ is the spatial image resolution of the detector array in a direction parallel to the Y-axis,
$\Delta Z_3$ is the spatial image resolution of the detector array in a direction parallel to the Z-axis,
$\psi$ is the pivot angle which ranges from about zero degrees to about ninety degrees,
$\alpha$ is the tilt angle which ranges from about zero degrees to about forty-five degrees,
$\Delta Y_1$ is a spacing between centers of the detector cells in a direction parallel to the Y-axis for a condition wherein $\psi$ equals ninety degrees and $\alpha$ equals zero degrees, and
$\Delta Z_1$ is a spacing between centers of the detector cells in a direction parallel to the Z-axis for a condition wherein $\psi$ equals ninety degrees and $\alpha$ equals zero degrees;

means for processing signals generated by the detector cells of the detector array to generate a human-perceivable image of the subject; and means for rotating the subject about a scan axis as the detector array and x-ray radiation source remain stationary, wherein the subject is disposed between the x-ray radiation source and the detector array at a location on or adjacent the scan axis, and wherein the scan axis is substantially parallel to the Z-axis.

* * * * *